US005800417A

United States Patent [19]

Goerg-Wood et al.

[11] Patent Number: 5,800,417
[45] Date of Patent: Sep. 1, 1998

[54] ABSORBENT COMPOSITION COMPRISING HYDROGEL-FORMING POLYMERIC MATERIAL AND FIBER BUNDLES

[76] Inventors: Kristin Ann Goerg-Wood, 2149 Michelle Ct., Apt. D; Franklin M. C. Chen, 1820 W. Glendale Ave., both of Appleton, Wis. 54914; Fung-jou Chen, 3216 White Birch La., Appleton, Wis. 54915

[21] Appl. No.: 571,005

[22] Filed: Dec. 12, 1995

[51] Int. Cl.$^6$ .............................. A61F 13/15; A61F 13/20
[52] U.S. Cl. ........................ 604/367; 604/368; 502/402
[58] Field of Search ................................. 604/368, 367, 604/369, 372, 374, 375, 376, 378; 502/402

[56] References Cited

U.S. PATENT DOCUMENTS

| H1639 | 3/1997 | Crainic | 604/368 |
|---|---|---|---|
| 4,036,679 | 7/1977 | Back et al. | 162/9 |
| 4,256,111 | 3/1981 | Lassen | 128/284 |
| 4,865,596 | 9/1989 | Weisman et al. | 604/368 |
| 4,883,021 | 11/1989 | Ducharme et al. | 119/1 |
| 4,883,478 | 11/1989 | Lerailler et al. | 604/360 |
| 5,188,624 | 2/1993 | Young, Sr. et al. | 604/378 |
| 5,330,457 | 7/1994 | Cohen | 604/368 |
| 5,334,177 | 8/1994 | Cohen | 604/368 |
| 5,509,914 | 4/1996 | Osborn, III | 604/368 |

FOREIGN PATENT DOCUMENTS

| 0 198 638 A2 | 10/1986 | European Pat. Off. |
| 0 339 461 A1 | 11/1989 | European Pat. Off. |
| 0 359 615 A1 | 3/1990 | European Pat. Off. |
| 0 443 627 A2 | 8/1991 | European Pat. Off. |
| 0 474 443 A2 | 3/1992 | European Pat. Off. |
| 0 532 002 A1 | 3/1993 | European Pat. Off. |
| 0 601 529 A1 | 6/1994 | European Pat. Off. |
| 2 246 373 | 1/1992 | United Kingdom. |
| WO 87/03208 A1 | 6/1987 | WIPO. |
| WO 94/23121 | 10/1994 | WIPO. |

OTHER PUBLICATIONS

Derwent World Patent Database abstract of JP 56-015,491 A: Description of Gosei Kagaku Kenkyusho, "Absorbent for Pitch Pulp Comprises Laminar Inorganic Material".
Derwent World Patent Database abstract of JP 5-059,362 A: Description of S. Kyoto, "Soil Conditioner For Dry Fields."
Patent Cooperation Treaty Search Report from the International Search Authority, International Application No. PCT/US 96/17961 dated Mar. 12, 1997.
"Fiber Bundles in Baled Flash Dried Pulp," UM 239, *1991 TAPPI Useful Methods*, pp. 38–39.
"Flake Content of Pulp," T 270 pm-88, Provisional Method—1988, *TAPPI* 1987, pp.1–2.
*Pulping Processes*, Sven A. Rydholm, "III. Screening and Cleaning," Interscience Publishers, 1965, pp. 738–749.

*Primary Examiner*—Robert A. Clarke
*Assistant Examiner*—Ki Yong O
*Attorney, Agent, or Firm*—John R. Schenian

[57] ABSTRACT

Disclosed is an absorbent composition comprising a hydrogel-forming polymeric material and fiber bundles, wherein the absorbent composition exhibits desired absorbent properties. The absorbent composition is suitable for use in absorbent structures and disposable absorbent products. The absorbent composition comprises a hydrogel-forming polymeric material in an amount of from about 5 to about 95 weight percent, and fiber bundles in an amount of from about 5 to about 95 weight percent; wherein all weight percents are based upon the total weight of the hydrogel-forming polymeric material and the fiber bundles in the absorbent composition; and wherein the absorbent composition exhibits an Absorbency Under Load value that is at least about 10 percent greater than the Absorbency Under Load value exhibited by an otherwise substantially identical absorbent composition that does not comprise the fiber bundles.

20 Claims, No Drawings

ABSORBENT COMPOSITION COMPRISING HYDROGEL-FORMING POLYMERIC MATERIAL AND FIBER BUNDLES

BACKGROUND OF THE INVENTION

1. Field of the Invention

The present invention relates to an absorbent composition suitable for use in absorbent structures and disposable absorbent products. More particularly, the present invention relates to an absorbent composition comprising a hydrogel-forming polymeric material and fiber bundles wherein the absorbent composition exhibits desired absorbent properties.

2. Description of the Related Art

The use of hydrogel-forming polymeric materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The absorbent materials described above generally have an absorbent capacity of at least about 10, preferably about 20, and often up to 100 times their weight in water. Clearly, incorporation of such absorbent materials in personal care products can reduce the overall bulk while increasing the absorbent capacity of such products.

Water-soluble polymers are often present in absorbent products. For example, feminine care absorbent products are designed to absorb menstrual fluid which contains proteins that are water soluble. In flushable products, water-soluble adhesives are often used to provide product functionality during use, but such adhesives are readily disintegrated when the product is placed in an excess of water, such as in a toilet bowl, after use. Even in conventional absorbent products for urine absorption, the un-crosslinked oligomers present in conventional polyacrylate superabsorbents are a source of water-soluble polymers.

Water-soluble polymers have now been found to generally be detrimental to the absorbency performance of the superabsorbent as well as the absorbent product in which such superabsorbent is used. The water-soluble polymers interfere with and generally depress the absorbency properties of the superabsorbent towards aqueous liquids. In addition, the water-soluble polymers interfere with the transport of an aqueous liquid within an absorbent product. Thus, it is desirable to remove, or at least suppress, the negative effects of the water-soluble polymers in-situ in an absorbent composition or product without sacrificing the overall absorbency performance of the absorbent composition or product.

SUMMARY OF THE INVENTION

In one aspect, the present invention concerns an absorbent composition comprising a hydrogel-forming polymeric material and fiber bundles wherein the absorbent composition exhibits desired absorbent properties. The absorbent composition is suitable for use in absorbent structures and disposable absorbent products.

In one embodiment of the present invention, an absorbent composition comprises a hydrogel-forming polymeric material in an amount of from about 5 to about 95 weight percent, and fiber bundles in an amount of from about 5 to about 95 weight percent; wherein all weight percents are based upon the total weight of the hydrogel-forming polymeric material and the fiber bundles in the absorbent composition; and wherein the absorbent composition exhibits an Absorbency Under Load value that is at least about 10 percent greater than the Absorbency Under Load value exhibited by an otherwise substantially identical absorbent composition that does not comprise the fiber bundles.

In another aspect, it is desirable to provide a thin, disposable absorbent product, such as an infant diaper, which product employs an absorbent structure having a relatively small volume and a relatively high concentration of hydrogel-forming polymeric material. Further, it is desirable to provide a disposable absorbent product which has a relatively small volume and a relatively high liquid-absorptive capacity.

In one embodiment, these goals are achieved in a disposable absorbent product comprising a topsheet, a backsheet attached to the topsheet, and an absorbent structure positioned between the topsheet and the backsheet, wherein the absorbent structure comprises an absorbent composition comprising hydrogel-forming polymeric material and fiber bundles, and wherein the absorbent composition exhibits desired absorbent properties.

DETAILED DESCRIPTION OF THE INVENTION

As used herein, "hydrogel-forming polymeric material" is meant to refer to a high-absorbency material commonly referred to as a superabsorbent material. Such high-absorbency materials are generally capable of absorbing an amount of a liquid, such as synthetic urine, a 0.9 weight percent aqueous saline solution, or body liquids such as menses, urine, or blood, at least about 10, suitably about 20, and up to about 100 times the weight of the superabsorbent material at the conditions under which the superabsorbent material is being used. Typical conditions include, for example, a temperature of between about 0° C. to about 100° C. and suitably ambient conditions, such as about 23° C. and about 30 to about 60 percent relative humidity. Upon absorption of the liquid, the superabsorbent material typically swells and forms a hydrogel.

The superabsorbent material may be formed from an organic hydrogel-forming polymeric material, which may include natural materials such as agar, pectin, and guar gum, as well as synthetic hydrogel-forming polymeric materials. Synthetic hydrogel-forming polymeric materials include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyridines. Other suitable hydrogel-forming polymeric materials include hydrolyzed acrylonitrile grafted starch, acrylic acid grafted starch, and isobutylene maleic anhydride copolymers, and mixtures thereof. The hydrogel-forming polymeric materials are preferably lightly crosslinked to render the material substantially water insoluble yet water swellable. Crosslinking may, for example, be by irradiation or covalent, ionic, van der Waals, or hydrogen bonding. Suitable hydrogel-forming polymeric materials are typically available from various commercial vendors, such as The Dow Chemical Company, Hoechst Celanese, Allied Colloids Limited, or Stockhausen, Inc.

Suitably, the hydrogel-forming polymeric material is in the form of particles which, in the unswollen state, have maximum cross-sectional diameters within the range of from about 50 micrometers to about 1000 micrometers, and more suitably within the range of from about 100 micrometers to about 800 micrometers, as determined by sieve analysis according to American Society for Testing and Materials (ASTM) test method D-1921. It is to be understood that the particles of hydrogel-forming polymeric material falling within the size ranges described above may comprise solid particles, porous particles, or agglomerated particles comprising many smaller particles agglomerated into particles falling within the described size ranges.

The hydrogel-forming polymeric material is present in the absorbent composition of the present invention in an amount effective to result in the absorbent composition being able to absorb a desired amount of liquid under desired conditions. The hydrogel-forming polymeric material is present in the absorbent composition of the present invention in an amount greater than 0 to less than 100 weight percent, beneficially from about 5 to about 95 weight percent, suitably from about 15 to about 85 weight percent, and more suitably from about 20 to about 80 weight percent, based on the total weight of the hydrogel-forming polymeric material and fiber bundles in the absorbent composition.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

As used herein, the term "fiber bundle" is meant to refer to a generally particulate material consisting essentially of entangled fibers. As such, the fiber bundle will also generally comprise capillaries or voids within the structure of the fiber bundle between the entangled fibers forming the fiber bundle. A fiber bundle may also be referred to by other terms known in the art such as fiber nits or fiber flakes. As will be appreciated by those skilled in the art, a fiber bundle will generally have an irregular, nonspherical shape. Furthermore, as will be appreciated by those skilled in the art, the fiber bundles comprising a fiber bundle sample will generally exhibit a range of sizes, since the production of fiber bundles will generally not result in uniform fiber bundles. As used herein, "equivalent fiber bundle particle size" is meant to be a measure of the equivalent diameter of a fiber bundle as if the fiber bundle was assumed to be spherically shaped. The equivalent fiber bundle particle size may be quantified, for example, by sieving a fiber bundle sample. Alternatively, the equivalent fiber bundle particle size for individual fiber bundles may be determined by an image analysis method wherein a fiber bundle sample is placed on a glass plate and a high-resolution picture is taken. From the measured area of a fiber bundle, the equivalent fiber bundle particle size can be calculated by assuming that the fiber bundle is circular across its cross-section.

Fiber bundles useful in the present invention have an equivalent particle size that is greater than about 150 micrometers and less than about 10,000 micrometers, beneficially greater than about 250 micrometers and less than about 5,000 micrometers, and suitably greater than about 300 micrometers and less than about 2,000 micrometers.

A wide variety of natural and synthetic fibers can be employed in the preparation of the fiber bundles useful in the absorbent composition of the present invention. Illustrative fibers include, but are not limited to, wood and wood products, such as wood pulp fibers, cellulose or cellulose acetate flocs, cotton linter flocs and the like, inorganic fibers, synthetic fibers such as nylon flocs, rayon flocs, polyacrylonitrile fibers, and the like. It is also possible to use mixtures of one or more natural fibers, or one or more synthetic fibers, or combinations of the two.

Suitable fibers are those which are wettable in nature. As used herein, the term "wettable" is meant to refer to a fiber or material which exhibits a water in air contact angle of less than 90°. Suitably, a wettable fiber refers to a fiber which exhibits a water in air contact angle of less than 90°, at a temperature between about 0° C. and about 100° C., and suitably at ambient conditions such as about 23° C.

However, nonwettable fibers can also be used. It is possible to treat the fiber surfaces by an appropriate method to render them more or less wettable. When surface-treated fibers are employed, the surface treatment is desirably nonfugitive; that is, the surface treatment desirably does not wash off the surface of the fiber with the first liquid insult or contact. For the purposes of this application, a surface treatment on a generally nonwettable fiber will be considered to be nonfugitive when a majority of the fibers demonstrate a water-in-air contact angle of less than 90° for three consecutive contact angle measurements, with drying between each measurement. That is, the same fiber is subjected to three separate contact angle determinations and, if all three of the contact angle determinations indicate a contact angle of water in air of less than 90°, the surface treatment on the fiber will be considered to be nonfugitive. If the surface treatment is fugitive, the surface treatment will tend to wash off of the fiber during the first contact angle measurement, thus, exposing the nonwettable surface of the underlying fiber and will demonstrate subsequent contact angle measurements greater than 90°. Beneficial wettability agents include polyalkylene glycols, such as polyethylene glycols. The wettability agent is used in an amount comprising beneficially less than about 5 weight percent, suitably less than about 3 weight percent, and more suitably less than about 2 weight percent of the total weight of the fiber being treated.

Fiber bundles generally occur naturally in processes for preparing fibers, such as in a pulping process, wherein some of the processed fibers become entangled. The amount of fiber bundles present in a pulp sample may be determined, for example, by the standardized TAPPI test procedure T 270 pm-88 (provisional method - 1988), "Flake content of pulp."

Fiber bundles, however, are generally undesirable, since the fiber bundles generally exhibit or impart properties on a final product different from those properties exhibited or imparted by unentangled fibers. In paper making, for example, fiber bundles are generally undesirable because the fiber bundles generally result in poor formation and poor surface smoothness of the paper. As such, any fiber bundles that survive a pulping process are generally removed from the substantially unentangled fibers by processes such as cleaning, screening, or low-consistency refining. Thus, fiber bundles may be collected as they are removed from typical fiber preparation processes. Alternatively, fiber bundles may be prepared directly by sufficiently entangling fibers in processes such as mixing or blending. Regardless of the method of preparation, the fiber bundles may be collected in either a dry or a wet state. If collected in a wet state, it may be desirable to dry the fiber bundles before use. Such drying may be accomplished by air-drying, oven-drying, or through-air-drying. Furthermore, it may be desirable or necessary to treat the fiber bundles so as to sufficiently separate the fiber bundles such that they have a desired particle size and/or may be effectively mixed with hydrogel-forming polymeric material.

The fiber bundles are present in the absorbent composition of the present invention in an amount effective to result in the absorbent composition being able to absorb a desired amount of liquid under desired conditions. The fiber bundles are present in the absorbent composition of the present invention in an amount greater than 0 to less than 100 weight percent, beneficially from about 5 to about 95 weight percent, suitably from about 15 to about 85 weight percent, and more suitably from about 20 to about 80 weight percent, based on the total weight of the hydrogel-forming polymeric material and fiber bundles in the absorbent composition.

The absorbent compositions of the present invention may generally be prepared, for example, by simply mixing together the desired amounts of hydrogel-forming polymeric material and fiber bundles. The mixing may be done by hand or by generally using any of a variety of mixing equipment known in the art. The mixing of hydrogel-forming polymeric material and fiber bundles may be done in a substantially dry state, such that hydrogel-forming polymeric material and fiber bundle particles do not substantially adhere to one another. Alternatively, the mixing of hydrogel-forming polymeric material and fiber bundles may be done in a substantially wet state, such that hydrogel-forming polymeric material and fiber bundle particles do substantially adhere to one another.

The absorbent compositions of the present invention have the ability to absorb a liquid, comprising a water-soluble polymer, while the absorbent composition is under an external pressure or load, herein referred to as Absorbency Under Load (AUL). Hydrogel-forming polymeric materials, such as polyacrylates, having a generally high ability to absorb while under a load, have been found to minimize the occurrence of gel-blocking when incorporated in absorbent products. The method by which the Absorbency Under Load is determined is set forth below in connection with the examples. The Absorbency Under Load values determined as set forth below and reported herein refer to the amount in grams of an aqueous solution, containing 0.9 weight percent sodium chloride and 3 weight percent of a polyvinyl alcohol, having an average molecular weight of about 141,000 and having an intrinsic viscosity of about 0.2 deciliter/gram, a gram of absorbent composition can absorb in 60 minutes under a load of about 0.3 pound per square inch (psi). As a general rule, it is desired that the absorbent composition of the present invention has an Absorbency Under Load value, for a load of about 0.3 psi, of at least about 8, beneficially of at least about 10, more beneficially of at least about 12, suitably of at least about 15, more suitably of at least about 20, and up to about 50 grams per gram.

An absorbent composition comprising both hydrogel-forming polymeric material and fiber bundled has surprisingly been found to exhibit improved absorbency properties as compared to the use of either the hydrogel-forming polymeric material or the fiber bundles alone when the liquid being absorbed comprises a water-soluble polymer. In particular, when an absorbent composition comprising both hydrogel-forming polymeric material and fiber bundles is contacted with an aqueous saline solution comprising about 3 weight percent polyvinyl alcohol, such an absorbent composition is able to absorb more of the aqueous solution, on a gram of solution absorbed per gram of absorbent composition basis, while the absorbent composition is under a pressure or load as compared to the amount of the aqueous solution absorbed under similar conditions by either the hydrogel-forming polymeric material or the fiber bundles alone.

As a general rule, it is desired that the absorbent composition of the present invention has an Absorbency Under Load value that is beneficially at least about 10 percent, more beneficially at least about 15 percent, suitably at least about 20 percent, more suitably at least about 25 percent, and most suitably at least about 40 percent greater than the Absorbency Under Load value exhibited by an otherwise substantially identical absorbent composition that does not comprise fiber bundles.

As used herein, the term "an otherwise substantially identical absorbent composition that does not comprise fiber bundles" and other similar terms are intended to refer to a control absorbent composition that is prepared using substantially identical materials and a substantially identical process as compared to an absorbent composition of the present invention, except that the control absorbent composition does not comprise or is not prepared with the fiber bundles described herein. As a result of not comprising the fiber bundles, the otherwise substantially identical absorbent composition generally will not exhibit the improved absorbency properties as described herein, such as an improved Absorbency Under Load value, as compared to the absorbent composition of the present invention.

As a general rule, it is desired that the hydrogel-forming polymeric material present in an absorbent composition of the present invention exhibits a calculated Absorbency Under Load value that is beneficially at least about 20 percent, more beneficially at least about 35 percent, suitably at least about 50 percent, and more suitably at least about 100 percent, greater than the Absorbency Under Load value exhibited by the hydrogel-forming polymeric material present in an otherwise substantially identical absorbent composition that does not comprise fiber bundles.

As used herein, the calculated Absorbency Under Load value for a hydrogel-forming polymeric material is intended to represent the individual contribution of the hydrogel-forming polymeric material to the Absorbency Under Load value of the total absorbent composition. Such a calculated Absorbency Under Load value for a hydrogel-forming polymeric material in an absorbent composition may be determined by: 1) taking the measured Absorbency Under Load value for a particular absorbent composition sample, 2) subtracting the value obtained by multiplying the weight percent of fiber bundles being used in the absorbent composition sample by the measured Absorbency Under Load value for when 100 weight percent fiber bundles are used, and 3) dividing by the weight percent of hydrogel-forming polymeric material being used. These calculations assume that the Absorbency Under Load contribution of the fiber bundles, on a relative basis, remains constant as the weight percent of the fiber bundles varies in the absorbent composition samples.

In general, the presence of water-soluble polymers in an aqueous solution has been found to interfere with the ability of a hydrogel-forming polymeric material to absorb the aqueous solution when the hydrogel-forming polymeric material is under an applied load. When blended with fiber bundles as described herein, however, the ability of a hydrogel-forming polymeric material to absorb an aqueous solution comprising water-soluble polymers has surprisingly been found to improve substantially. In general, the fiber bundles are believed to absorb and effectively trap the water-soluble polymers present in the aqueous solution so that such water-soluble polymers are not able to interfere with the absorption of the remainder of the aqueous solution by the hydrogel-forming polymeric material. Furthermore, the capillaries within the structure of the fiber bundles are generally not responsible for distribution or transport of an aqueous liquid within an absorbent structure or product in which the absorbent composition comprising the fiber bundles is used. As such, the absorption by the fiber bundles of water-soluble polymers will generally not negatively affect the distribution of the aqueous liquid within the absorbent structure or product. In fact, just the opposite generally occurs. Because the water-soluble polymers are generally absorbed by the fiber bundles, such water-soluble polymers are removed from the aqueous solution being absorbed by the absorbent composition so that such water-soluble polymers are not present to interfere with the distribution of the aqueous solution within an absorbent structure or product.

In one embodiment of the present invention, a disposable absorbent product is provided, which disposable absorbent product comprises a liquid-permeable topsheet, a backsheet attached to the topsheet, and an absorbent structure positioned between the topsheet and the backsheet wherein the absorbent structure comprises an absorbent composition comprising a hydrogel-forming polymeric material and fiber bundles, wherein the absorbent composition exhibits desired absorbent properties.

Those skilled in the art will recognize materials suitable for use as the topsheet and backsheet. Examples of materials suitable for use as the topsheet are liquid-permeable materials, such as spunbonded polypropylene or polyethylene having a basis weight of from about 15 to about 25 grams per square meter. Examples of materials suitable for use as the backsheet are liquid-impervious materials, such as polyolefin films, as well as vapor-pervious materials, such as microporous polyolefin films.

The absorbent composition of the present invention will generally be employed in a disposable absorbent product in the form of an absorbent structure. Such an absorbent structure will generally comprise a fibrous matrix into which, for example, the absorbent composition is dispersed such that the fibrous matrix constrains or entraps the absorbent composition.

The fibrous matrix may be formed by air-laying fibers, through a spunbond or meltblown process, a carding process, a wet-laid process, or through essentially any other means known to those skilled in the art for forming a fibrous matrix. Methods of incorporating the absorbent composition of the present invention into a fibrous matrix are known to those skilled in the art. Suitable methods include incorporating the absorbent composition into the matrix during formation of the matrix, such as by air-laying the fibers of the fibrous matrix and the absorbent composition at the same time or wet-laying the fibers of the fibrous matrix and the absorbent composition at the same time. Alternatively, it is possible to apply the absorbent composition to the fibrous matrix after formation of the fibrous matrix. Other methods include sandwiching the absorbent composition between two sheets of material, at least one of which is fibrous and liquid permeable. The absorbent composition may be generally uniformly located between the two sheets of material or may be located in discrete pockets formed by the two sheets. The absorbent composition may be distributed in the individual layers in a generally uniform manner or may be present in the fibrous layers as a layer or other nonuniform distribution.

The fibrous matrix may be in the form of a single, integrally formed layer or of a composite comprising multiple layers. If the fibrous matrix comprises multiple layers, the layers are preferably in liquid communication with one another such that a liquid present in one fibrous layer can flow or be transported to the other fibrous layer. For example, the fibrous layers may be separated by cellulosic tissue wrap sheets known to those skilled in the art.

When the fibrous matrix comprises a single, integrally formed layer, the concentration of absorbent composition may increase along the thickness of the fibrous matrix in a gradual, nonstepwise fashion or in a more stepwise fashion. Similarly, the density may decrease through the thickness in a nonstepwise manner or in a stepwise manner. The absorbent structures of the present invention may generally be of any size or dimension as long as the absorbent structure exhibits the desired absorbent characteristics.

The absorbent structure of the present invention may also be used or combined with other absorbent structures, with the absorbent structure of the present invention being used as a separate layer or as an individual zone or area within a larger, composite absorbent structure. The absorbent structure of the present invention may be combined with other absorbent structures by methods well known to those skilled in the art, such as by using adhesives or simply by layering the different structures together and holding together the composite structures with, for example, tissue.

The absorbent structures according to the present invention are suited to absorb many liquids, such as water, saline, and synthetic urine, and body liquids such as urine, menses, and blood, and are suited for use in disposable absorbent products such as diapers, adult incontinent products, and bed pads; in catamenial devices such as sanitary napkins, and tampons; and in other absorbent products such as wipes, bibs, wound dressings, and surgical capes or drapes.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

Test Methods

Absorbency Under Load

The Absorbency Under Load (AUL) is a test which measures the ability of an absorbent material to absorb a liquid (a 0.9 weight percent solution of sodium chloride and 3 weight percent of polyvinyl alcohol, having an average molecular weight of about 141,000 and having an intrinsic viscosity of about 0.2 deciliter/gram in distilled water) while under an applied load or restraining force of about 0.3 pound per square inch for a period of about 60 minutes.

A sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

To carry out the test, a 0.160 gram sample of the absorbent material is placed into the sample cup. The sample is then covered with a plastic spacer disc, weighing 4.4 grams and having a diameter of about 0.995 inch, which serves to protect the sample from being disturbed during the test and also to uniformly apply a load on the entire sample. A 100 gram weight is then placed on top of the spacer disc, thereby applying a load of about 0.3 pound per square inch to the sample material. The sample cup, with material sample, spacer disc, and 100 gram weight, is then weighed to get its dry weight.

The sample cup is placed in a Petri dish. A sufficient amount of saline/polyvinyl alcohol solution is added to the Petri dish (50–100 milliliters) to begin the test. The sample cup is kept in the Petri dish for about 60 minutes after which it is removed, lightly blotted with a paper towel to remove any free solution droplets adhering to the sample cup, and then weighed.

The AUL is calculated by determining the weight difference between the sample cup before and after the test, the weight difference being the amount of solution absorbed by the material sample. The weight of saline/polyvinyl alcohol solution absorbed after about 60 minutes is the AUL value expressed as grams of saline/polyvinyl alcohol solution absorbed per gram of sample material.

EXAMPLES

Absorbent compositions were prepared comprising a hydrogel-forming polymeric material and fiber bundles. Control compositions were prepared comprising only a hydrogel-forming polymeric material or only fiber bundles, respectively.

For Samples 1–4, 6, 7 and 8, a poly(acrylic acid) high-absorbency material, commercially available from Stockhausen, Inc., under the trade designation FAVOR SAB 870 M polyacrylate material, is used as the hydrogel-forming polymeric material. For Sample 5, a poly(acrylic acid) high-absorbency material, commercially available from Hoechst Celanese under the trade designation SAN-WET IM-1000 polyacrylate material, is used as the hydrogel-forming polymeric material.

The fiber bundles are prepared as follows: About 100 grams of a wet pulp is prepared by separating, by hand, a dry pulp of a starting material into about one-half inch by one-half inch pieces and then spraying with water until the desired consistency of the wet pulp is obtained. In the case of a rayon wet pulp, the consistency of the wet pulp is about 15 weight percent fibers. In the case of other fibers, the consistency of the wet pulp is about 20 weight percent fibers. The wet pulp is then mixed in a 5 quart Hobart mixer for about 1.5 hours. The mixed wet pulp is then spread on a flat surface and allowed to air-dry at ambient conditions of about 70° F. and about 30 to about 60 percent relative humidity.

For Samples 1 and 8, paper-grade loblolly pine cellulose, prepared using a fully-bleached kraft process, is the material used to prepare the fiber bundles. The prepared fiber bundles are found, as determined by image analysis, to have a maximum equivalent particle size of about 4960 micrometers and a mean equivalent particle size of about 1960 micrometers, based on fiber bundles having an equivalent particle size greater than about 300 micrometers.

For Sample 2, rayon, in the form of 0.125 inch long, 3 denier, fibers, is the material used to prepare the fiber bundles. The prepared fiber bundles are found, as determined by image analysis, to have a maximum equivalent particle size of about 9220 micrometers and a mean equivalent particle size of about 3780 micrometers, based on fiber bundles having an equivalent particle size greater than about 300 micrometers.

For Sample 3, bagasse, a non-woody fiber derived from sugar-cane, prepared using a soda pulped, bleached process, is the material used to prepare the fiber bundles. The prepared fiber bundles are found, as determined by image analysis, to have a maximum equivalent particle size of about 1800 micrometers, and a mean equivalent particle size of about 820 micrometers, based on fiber bundles having an equivalent particle size greater than about 300 micrometers.

For Samples 4–7, paper-grade hardwood eucalyptus, prepared using a fully-bleached kraft process, is the material used to prepare the fiber bundles. The prepared fiber bundles are found, as determined by image analysis, to have a maximum equivalent particle size of about 1860 micrometers and a mean equivalent particle size of about 795 micrometers, based on fiber bundles having an equivalent particle size greater than about 300 micrometers.

The absorbent compositions are prepared in the sample cup used to evaluate the Absorbency Under Load values by first placing the hydrogel-forming polymeric material into the sample cup, adding the fiber bundles as needed to form a mixture having a total weight of about 0.160 gram, and lightly mixing the materials together. The relative amounts of fiber bundles and hydrogel-forming polymeric material used in each sample are shown in Table 1. The percent fiber shown is given as a weight percent based on the total weight of fiber bundles and hydrogel-forming polymeric material used in the mixture of each sample.

The samples were evaluated for Absorbency Under Load according to the Test Method described herein. In Samples 1–5 and 8, the Absorbency Under Load was measured using a 0.9 weight percent solution of sodium chloride and 3 weight percent of a polyvinyl alcohol, having an average molecular weight, as determined by light scattering studies, of about 141,000 and having an intrinsic viscosity of about 0.2 deciliter/gram, commercially available from Nippon Synthetic Chemical Industrial Co. under the trade designation Gohsenol KZ-06 polyvinyl alcohol, in distilled water. In Sample 6, the Absorbency Under Load was measured using a 0.9 weight percent solution of sodium chloride and 1 weight percent of a polyvinyl alcohol (Nippon Synthetic Chemical Industrial Co.'s Gohsenol KZ-06 polyvinyl alcohol) in distilled water. In Sample 7, the Absorbency Under Load was measured using a 0.9 weight percent solution of sodium chloride and 3 weight percent of a hydroxypropyl cellulose, commercially available from Hercules, Inc. under the trade designation KLUCEL LF hydroxypropyl cellulose, having an average molecular weight of about 116,000 and having an intrinsic viscosity of about 0.98 deciliter/gram, in distilled water. The results of these evaluations are shown in Table 1 under the heading Measured AUL.

In Table 1, the column headed Calculated AUL represents a calculated AUL value for each sample based upon the Measured AUL values within each sample for when 100 weight percent hydrogel-forming polymeric material is used and when 100 weight percent fiber bundles are used. As such, the Calculated AUL is determined by adding together the values calculated by 1) multiplying the weight percent of hydrogel-forming polymeric material being used by the Measured AUL value for when 100 weight percent hydrogel-forming polymeric material is used and 2) multiplying the weight percent of fiber bundles being used by the Measured AUL value for when 100 weight percent fiber bundles are used.

In Table 1, the column headed HFPM AUL represents a calculated AUL value for the AUL contribution of the hydrogel-forming polymeric material in the absorbent composition. This HFPM AUL value is determined by: 1) taking the Measured AUL value for a particular sample, 2) subtracting the value obtained by multiplying the weight percent of fiber bundles being used by the Measured AUL value for when 100 weight percent fiber bundles are used, and 3) dividing by the weight percent of hydrogel-forming polymeric material being used.

Similarly, the column headed HFPM AUL Increase in Table 1 represents the percent increase in the calculated AUL value for the AUL contribution of the hydrogel-forming polymeric material in the absorbent composition, using as the comparison value the HFPM AUL value for when 100 weight percent hydrogel-forming polymeric material is used.

These calculations assume that the AUL contribution of the fiber bundles, on a relative basis, remains constant as the weight percent of the fiber bundles varies in the absorbent composition samples. With this assumption, the HFPM AUL and HFPM AUL Increase calculations show that, as more fiber bundles are used, the hydrogel-forming polymeric material is able to absorb more of the aqueous solution and is, thus, used more efficiently. This phenomenon is believed to occur because the fiber bundles absorb and trap the water-soluble polymers present in the aqueous solution, thus, preventing such water-soluble polymers from interfering with the absorption of the aqueous solution by the hydrogel-forming polymeric material.

As control samples, absorbent compositions comprising only hydrogel-forming polymeric material is tested for Absorbency Under Load using, however, a 0.9 weight percent solution of sodium chloride in distilled water. As such, essentially no water-soluble polymer is present in the aqueous solution used to evaluate these control absorbent compositions. The FAVOR SAB 870 M hydrogel-forming polymeric material exhibits a control AUL value of about 16.2 grams per gram. The SANWET IM-1000 hydrogel-forming polymeric material exhibits a control AUL value of about 7.1 grams per gram.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

TABLE 1

| Sample No. | Percent Fiber | Measured AUL (g/g) | Calc AUL (g/g) | HFPM AUL (g/g) | HFPM AUL Increase (%) |
|---|---|---|---|---|---|
| 1 | 0 | 5.4 | 5.4 | 5.4 | 0 |
|   | 25 | 7.9 | 5.5 | 8.6 | 59 |
|   | 50 | 8.7 | 5.6 | 11.7 | 117 |
|   | 75 | 9.9 | 5.6 | 22.5 | 317 |
|   | 100 | 5.7 | 5.7 | — | — |
| 2 | 0 | 5.4 | 5.4 | 5.4 | 0 |
|   | 80 | 6.3 | 5.1 | 11.5 | 113 |
|   | 100 | 5.0 | 5.0 | — | — |
| 3 | 0 | 5.7 | 5.7 | 5.7 | 0 |
|   | 25 | 8.7 | 6.0 | 9.4 | 65 |
|   | 50 | 9.6 | 6.2 | 12.5 | 119 |
|   | 75 | 9.7 | 6.5 | 18.7 | 228 |
|   | 100 | 6.7 | 6.7 | — | — |
| 4 | 0 | 5.9 | 5.9 | 5.9 | 0 |
|   | 75 | 9.4 | 6.1 | 19.0 | 222 |
|   | 100 | 6.2 | 6.2 | — | — |
| 5 | 0 | 6.0 | 6.0 | 6.0 | 0 |
|   | 75 | 9.0 | 6.2 | 17.4 | 190 |
|   | 100 | 6.2 | 6.2 | — | — |
| 6 | 0 | 7.3 | 7.3 | 7.3 | 0 |
|   | 75 | 9.4 | 5.7 | 22.0 | 201 |
|   | 100 | 5.2 | 5.2 | — | — |
| 7 | 0 | 6.1 | 6.1 | 6.1 | 0 |
|   | 75 | 9.2 | 6.4 | 17.3 | 184 |
|   | 100 | 6.5 | 6.5 | — | — |
| 8 | 0 | 7.2 | 7.2 | 7.2 | 0 |
|   | 5 | 8.8 | 7.2 | 8.9 | 23 |
|   | 10 | 8.8 | 7.2 | 8.9 | 24 |
|   | 15 | 9.8 | 7.3 | 10.2 | 39 |
|   | 20 | 10.1 | 7.3 | 10.8 | 48 |
|   | 25 | 10.3 | 7.3 | 11.2 | 53 |
|   | 75 | 9.1 | 7.4 | 13.9 | 88 |
|   | 80 | 9.1 | 7.4 | 15.3 | 107 |
|   | 85 | 9.1 | 7.5 | 18.1 | 141 |
|   | 90 | 8.1 | 7.5 | 13.5 | 81 |
|   | 95 | 8.1 | 7.5 | 18.8 | 150 |
|   | 100 | 7.5 | 7.5 | — | — |

What is claimed is:

1. An absorbent composition mixture comprising:
   a. a hydrogel-forming polymeric material in an amount of from about 5 to about 95 weight percent; and
   b. fiber bundles in an amount of from about 5 to about 95 weight percent, wherein the fiber bundles are a Particulate material consisting essentially of entangled fibers that have an equivalent particle size that is greater than about 150 micrometers and less than about 10,000 micrometers, wherein all weight percents are based upon the total weight of the hydrogel-forming polymeric material and the fiber bundles in the absorbent composition, and wherein the absorbent composition exhibits an Absorbency Under Load value that is at least about 10 percent greater than the Absorbency Under Load value exhibited by an otherwise substantially identical absorbent composition that does not comprise the fiber bundles.

2. The absorbent composition of claim 1 wherein the hydrogel-forming polymeric material is present in the absorbent composition in an amount of from about 15 weight percent to about 85 weight percent, and the fiber bundles are present in the absorbent composition in an amount of from about 15 weight percent to about 85 weight percent.

3. The absorbent composition of claim 2 wherein the hydrogel-forming polymeric material is present in the absorbent composition in an amount of from about 20 weight percent to about 80 weight percent, and the fiber bundles are present in the absorbent composition in an amount of from about 20 weight percent to about 80 weight percent.

4. The absorbent composition of claim 1 wherein the absorbent composition exhibits an Absorbency Under Load value greater than about 8 grams per gram.

5. The absorbent composition of claim 4 wherein the absorbent composition exhibits an Absorbency Under Load value greater than about 10 grams per gram.

6. The absorbent composition of claim 5 wherein the absorbent composition exhibits an Absorbency Under Load value greater than about 12 grams per gram.

7. The absorbent composition of claim 1 wherein the absorbent composition exhibits an Absorbency Under Load value that is at least about 15 percent greater than the Absorbency Under Load value exhibited by on otherwise substantially identical absorbent composition that does not comprise fiber bundles.

8. The absorbent composition of claim 7 wherein the absorbent composition exhibits an Absorbency Under Load value that is at least about 20 percent greater than the Absorbency Under Load value exhibited by on otherwise substantially identical absorbent composition that does not comprise fiber bundles.

9. The absorbent composition of claim 8 wherein the absorbent composition exhibits an Absorbency Under Load value that is at least about 25 percent greater than the Absorbency Under Load value exhibited by on otherwise substantially identical absorbent composition that does not comprise fiber bundles.

10. The absorbent composition of claim 9 wherein the absorbent composition exhibits an Absorbency Under Load value that is at least about 40 percent greater than the Absorbency Under Load value exhibited by on otherwise substantially identical absorbent composition that does not comprise fiber bundles.

11. An absorbent composition mixture comprising:
   a. a hydrogel-forming polymeric material in an amount of from about 15 to about 85 weight percent; and
   b. fiber bundles in an amount of from about 15 to about 85 weight percent, wherein the fiber bundles are a particulate material consisting essentially of entangled fibers that have an equivalent particle size that is greater than about 150 micrometers and less than about 10,000 micrometers, wherein all weight percents are based upon the total weight of the hydrogel-forming polymeric material and the fiber bundles in the absorbent composition, and wherein the absorbent composition exhibits an Absorbency Under Load value that is at least about 25 percent greater than the Absorbency Under Load value exhibited by an otherwise substantially identical absorbent composition that does not comprise the fiber bundles.

12. A disposable absorbent product comprising a liquid-permeable topsheet, a backsheet attached to the topsheet, and an absorbent structure positioned between the topsheet and the backsheet, wherein the absorbent structure comprises an absorbent composition mixture comprising:
   a. a hydrogel-forming polymeric material in an amount of from about 5 to about 95 weight percent; and
   b. fiber bundles in an amount of from about 5 to about 95 weight percent, wherein the fiber bundles are a particulate material consisting essentially of entangled fibers that have an equivalent particle size that is greater than about 150 micrometers and less than about 10,000 micrometers, wherein all weight percents are based upon the total weight of the hydrogel-forming polymeric material and the fiber bundles in the absorbent composition, and wherein the absorbent composition exhibits an Absorbency Under Load value that is at least about 10 percent greater than the Absorbency Under Load value exhibited by an otherwise substantially identical absorbent composition that does not comprise the fiber bundles.

13. The disposable absorbent product of claim 12 wherein the hydrogel-forming polymeric material is present in the absorbent composition in an amount of from about 15 weight percent to about 85 weight percent, and the fiber bundles are present in the absorbent composition in an amount of from about 15 weight percent to about 85 weight percent.

14. The disposable absorbent product of claim 13 wherein the hydrogel-forming polymeric material is present in the absorbent composition in an amount of from about 20 weight percent to about 80 weight percent, and the fiber bundles are present in the absorbent composition in an amount of from about 20 weight percent to about 80 weight percent.

15. The disposable absorbent product of claim 12 wherein the absorbent composition exhibits an Absorbency Under Load value greater than about 8 grams per gram.

16. The disposable absorbent product of claim 15 wherein the absorbent composition exhibits an Absorbency Under Load value greater than about 10 grams per gram.

17. The disposable absorbent product of claim 12 wherein the absorbent composition exhibits an Absorbency Under Load value that is at least about 15 percent greater than the Absorbency Under Load value exhibited by on otherwise substantially identical absorbent composition that does not comprise fiber bundles.

18. The disposable absorbent product of claim 17 wherein the absorbent composition exhibits an Absorbency Under Load value that is at least about 20 percent greater than the Absorbency Under Load value exhibited by on otherwise substantially identical absorbent composition that does not comprise fiber bundles.

19. The disposable absorbent product of claim 18 wherein the absorbent composition exhibits an Absorbency Under Load value that is at least about 25 percent greater than the Absorbency Under Load value exhibited by on otherwise substantially identical absorbent composition that does not comprise fiber bundles.

20. A disposable absorbent product comprising a liquid-permeable topsheet, a backsheet attached to the topsheet, and an absorbent structure positioned between the topsheet and the backsheet, wherein the absorbent structure comprises an absorbent composition mixture comprising:
   a. a hydrogel-forming polymeric material in an amount of from about 15 to about 85 weight percent; and
   b. fiber bundles in an amount of from about 15 to about 85 weight percent, wherein the fiber bundles are a particulate material consisting essentially of entangled fibers that have an equivalent particle size that is greater than about 150 micrometers and less than about 10,000 micrometers, wherein all weight percents are based upon the total weight of the hydrogel-forming polymeric material and the fiber bundles in the absorbent composition, and wherein the absorbent composition exhibits an Absorbency Under Load value that is at least about 25 percent greater than the Absorbency Under Load value exhibited by an otherwise substantially identical absorbent composition that does not comprise the fiber bundles.

* * * * *